US 6,621,915 B1

(12) United States Patent
Chen et al.

(10) Patent No.: US 6,621,915 B1
(45) Date of Patent: Sep. 16, 2003

(54) METHOD AND SYSTEM INSPECTING ON-LINE COTTON WEB HOMOGENEITY BY DIGITAL IMAGE PROCESSING

(75) Inventors: Hung-Jen Chen, Taichung (TW); Hsin-Chung Lien, Taipei (TW); Chih-Hua Liu, Chung-Li (TW); Ding-Kuo Huang, Chung-Li (TW)

(73) Assignee: China Textile Institute, Taipei (TW)

( * ) Notice: Subject to any disclaimer, the term of this patent is extended or adjusted under 35 U.S.C. 154(b) by 0 days.

(21) Appl. No.: 09/515,212

(22) Filed: Feb. 29, 2000

(51) Int. Cl.⁷ .............................................. G06K 9/100
(52) U.S. Cl. .................... 382/111; 356/238.1; 700/130
(58) Field of Search ................... 382/111, 110, 382/112, 108, 109; 356/367, 238.1, 238.2, 238.3, 239.1, 429; 700/135, 143, 130, 131, 132, 133, 134, 142, 144

(56) References Cited

U.S. PATENT DOCUMENTS

| | | | | |
|---|---|---|---|---|
| 5,333,111 A | * | 7/1994 | Chaiken et al. | 700/135 |
| 5,383,135 A | * | 1/1995 | Shofner et al. | 700/143 |
| 5,598,266 A | * | 1/1997 | Cornuejols | 356/367 |

* cited by examiner

*Primary Examiner*—Jayanti K. Patel
*Assistant Examiner*—Seyed Azarian
(74) *Attorney, Agent, or Firm*—Rosenberg, Klein & Lee

(57) ABSTRACT

The present invention disclosed a method and system inspecting cotton web homogeneity by a digital image processing technique, in particular, for an on-line cotton web homogeneity test. It uses optical principles in conjunction with a charge coupled device type camera to find a theoretical equation indicating the correlation between the transmittance of cotton webs and basic weights (weights per unit area). Next, the invention makes use of a numerical analysis method to find the optimal approximation equation representing a relationship between measured transmittance and basic weights of cotton webs. When executing an on-line inspection, a system according to the invention detects the transmittance of cotton webs by means of the computer controlled visual device and then calculates correlated data of cotton web homogeneity variations according to the approximation equation acquired previously. Besides, the system can monitor production operation and detect any abnormal conditions or periodical variations in production through a quick Fourier transformation of homogeneity variations. The invention can be applied to on-line web homogeneity tests either for cotton webs or for other materials like paper or non-woven fabric.

15 Claims, 7 Drawing Sheets

METHOD AND SYSTEM INSPECTING ON-LINE COTTON WEB HOMOGENEITY BY DIGITAL IMAGE PROCESSING

BACKGROUND OF THE INVENTION

This present invention relates to a method and system that uses a digital image processing technique to examine cotton web homogeneity and monitor the operation of production equipment. Hence the invention is pertinent to the technical field of promoting production efficiency and product quality. The purpose of examining the homogeneity of cotton webs is to find the variations in density and the weight per unit area (called basic weight) in a production period to see if any abnormal operations occur. If the basic weight varies slightly, cotton webs has better homogeneity. Hence the quality of cotton webs can be promoted by controlling its homogeneity. The inspection methods according to a prior art are generally divided into two groups:

1. Detect the thickness of cotton webs by floating pressurized rollers and convert measured thickness data into weights and then examine the variations in weight. One of the disadvantages of such a method is that the direct contact between rollers and cotton webs may cause damages to cotton webs, in particular, in a lightweight cotton web test.

2. Detect homogeneity by radioactive rays ($\alpha$ rays or $\beta$ rays). The radioactive rays are detrimental to human bodies and so most tests use spot measurement to evaluate the homogeneity of cotton webs. Generally homogeneity is judged by weights per unit area. Weight changes on spots do not have sufficient representation for the variations in the whole area. Thus it affects the correctness of results.

In view of the above-mentioned problems, the homogeneity test method proposed by the inventor is a non-contact measurement one that eliminates the possibility of injury to the physical properties of cotton webs. Adjusting the aperture of cameras can change sampled areas. As a result the influence of local density variations on the evaluation of overall homogeneity can be minimized. Besides, the measurement correctness can be promoted and there is no harm to human bodies and physical properties of cotton webs.

The present invention will be now described according to its preferred embodiments, with particular reference to the system configuration diagrams and the schematic structural figures of the accompanying drawings, in which.

DETAILED DESCRIPTION OF THE INVENTION

Figure 1:
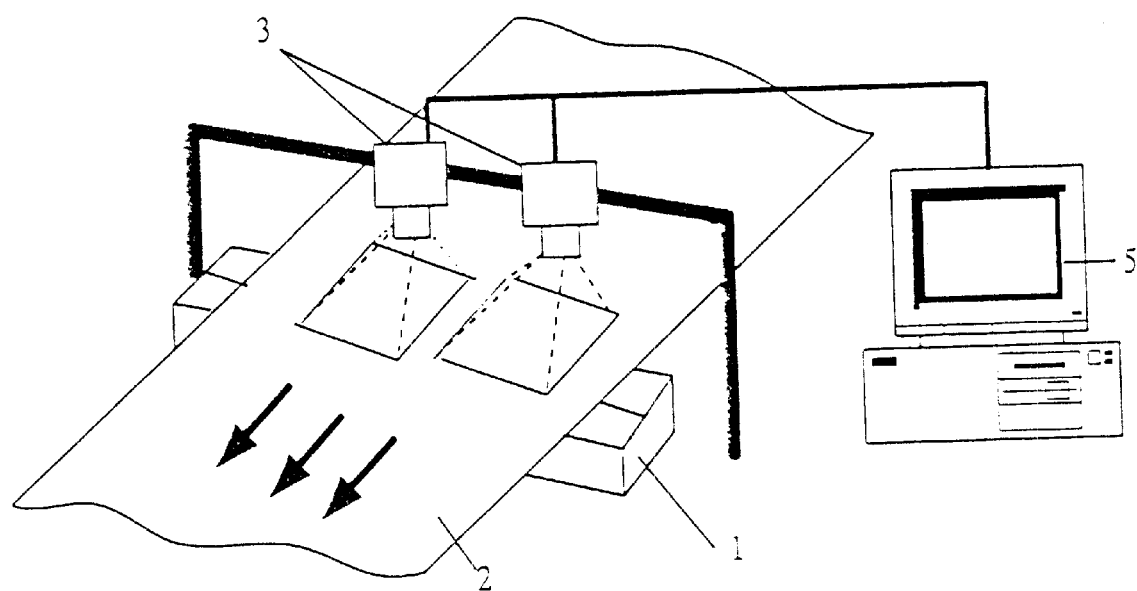
FIG. 1 is a schematic diagram indicating the arrangement of the components of an inspection system according to the invention.
Figure 2:
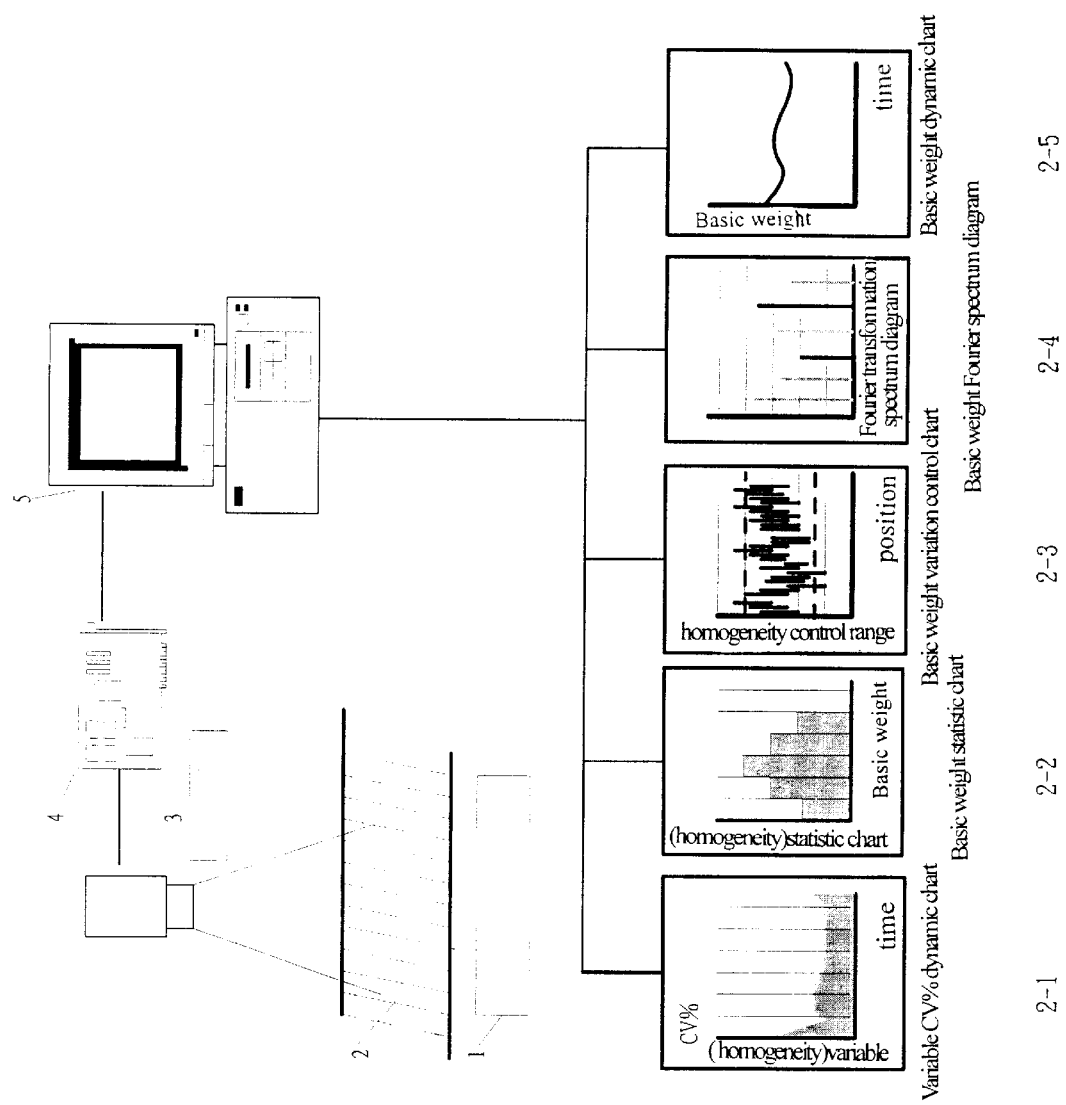
FIG. 2 is a schematic drawing showing the overall configuration of the system of FIG. 1.
Figure 3:
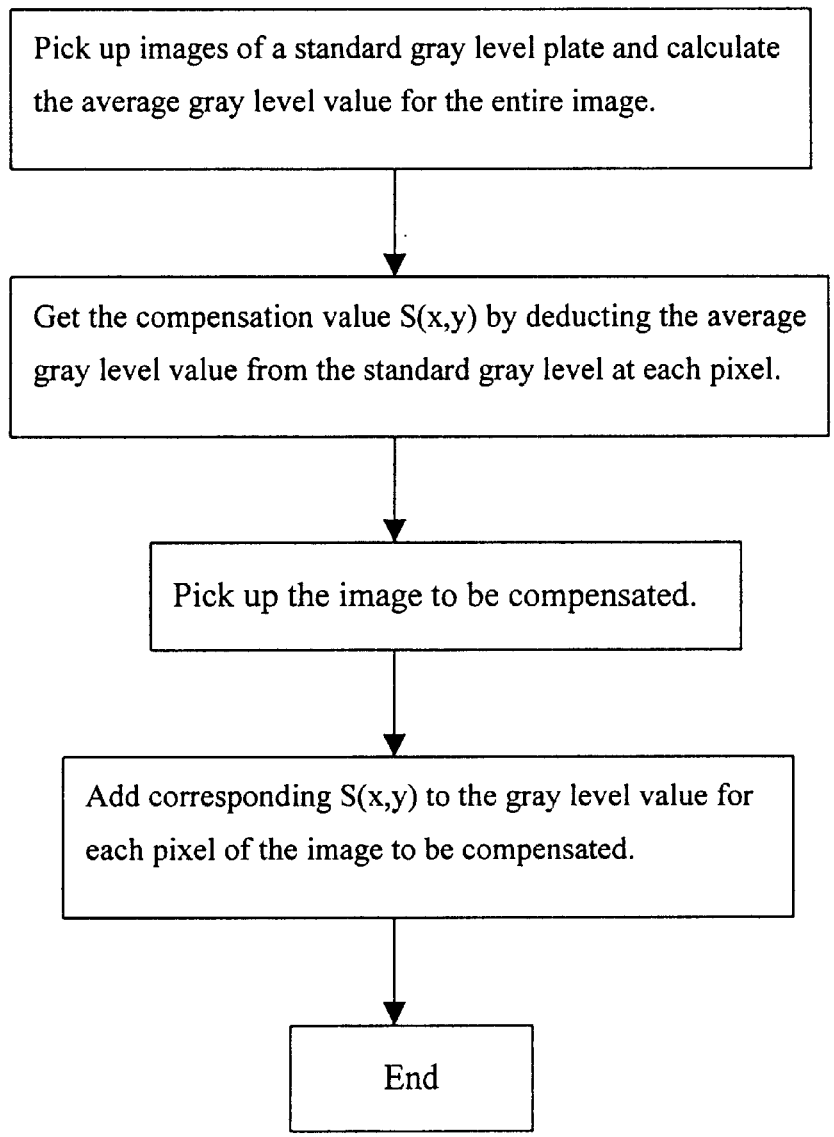
FIG. 3 is a flow chart illustrating the methodology of illumination compensation according to the invention.
Figure 4:
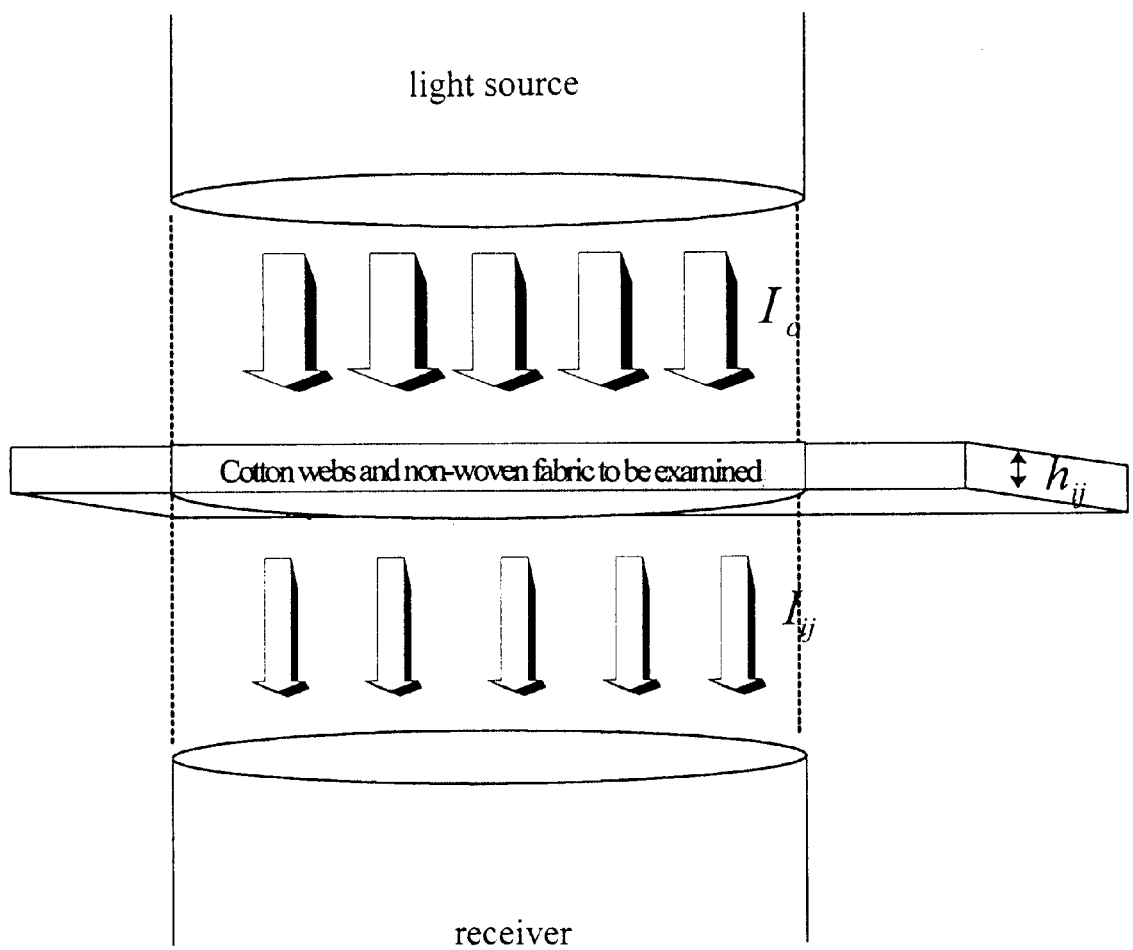
FIG. 4 is a schematic drawing illustrating the principle of transmittance measurement according to the invention.

The inspection procedures according to the invention will be detailed as follows. The method and system of the invention are used to examine the homogeneity of cotton webs. The system comprises a light source 1, a charge-coupled device (CCD) type camera 3, an image pickup card 4, and a personal computer 5. The CCD type camera 3 is used to take the image of an object to be examined, the image pickup card 4 can store the image and the personal computer 5 calculates and analyzes the image and stores the result and displays it on the screen. The invention uses such an inspection system in conjunction with the methodology of the invention to examine the homogeneity of cotton webs. It uses optical principles (referring to FIG. 4) in conjunction with a camera 3 and a light source 1 to find the correlation between the transmittance of cotton webs and the basic weights (referring to FIG. 5). Furthermore, it makes use of a numerical analysis method to find a mathematical approximation equation representing such correlation (referring to FIG. 6). When executing an on-line inspection, the system detects the transmittance of cotton webs by using a computer controlled visual device and gets the variations in basic weights through converting the detected transmittance into basic weights by the mathematical approximation equation. The data resulted from the calculation includes a CV % dynamic curve chart 2-1, a basic weight statistic chart 2-2, a basic weight control chart 2-3, and a basic weight dynamic curve chart 2-5. The computer further generates a Fourier transformation spectrum diagram 2-4 on the basis of calculated homogeneity variations. In this way, the system can monitor the operation of machines and homogeneity variations in a production period. The principles of this invention are detailed as follows.

Figure 5:
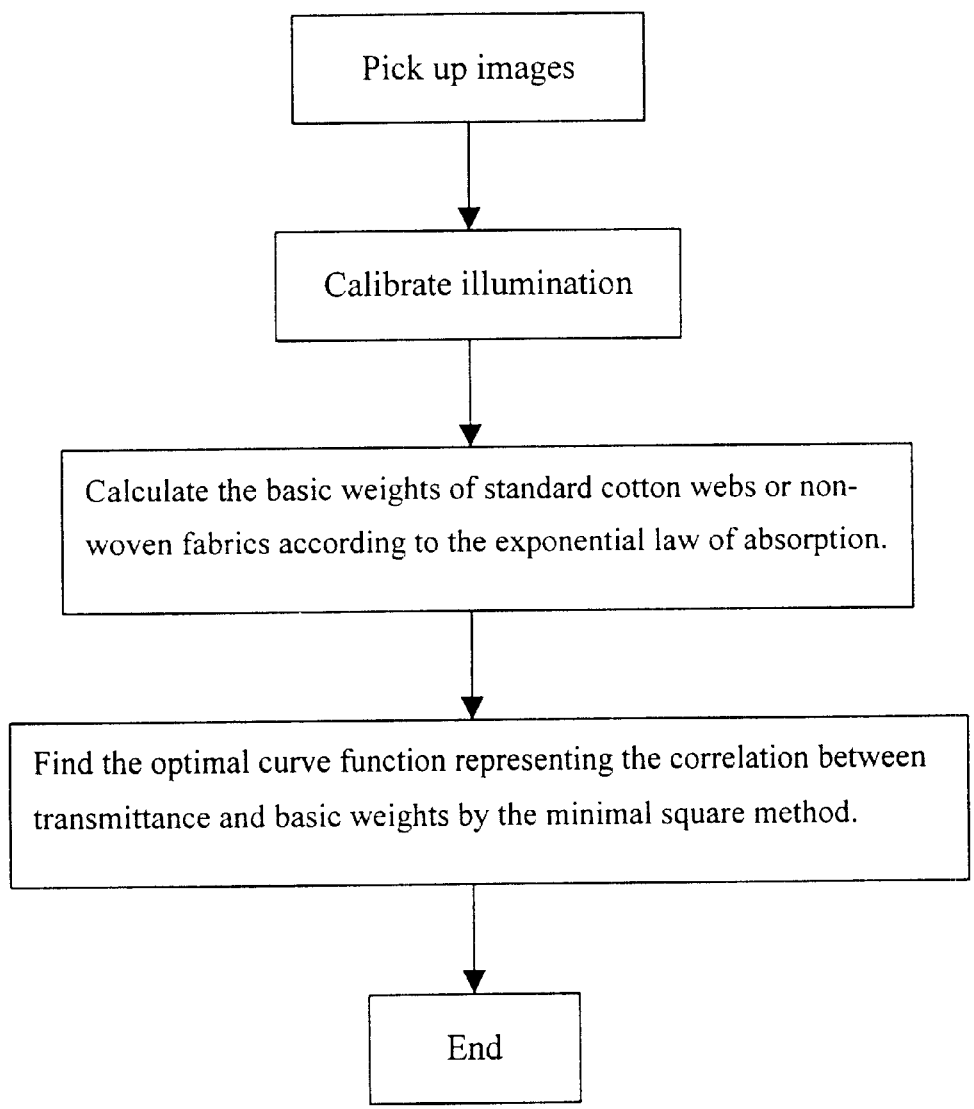
FIG. 5 is a flow chart depicting the calculation procedure of the correlation between basic weights and gray levels according to the present invention.

(1) Light source compensation (referring to FIG. 5)

The purpose is to compensate the unevenness of illumination due to lighting or CCD cameras that may results in inhomogeneous brightness. The invention makes use of a sample having standard gray levels and takes its image as a standard image (with a area a×b). The gray level value of a pixel is h(x, y). The average gray level value $Gray_{AVE}$ of the standard image can be obtained from the pixel gray level values The compensating gray level value S(x, y) is obtained by deducing the average gray level value $Gray_{AVE}$ from a standard gray level value of a pixel.

The procedure is denoted by:

$$Gray_{AVE} = \frac{1}{a \cdot b}\sum_{x=1}^{x=a}\sum_{y=a}^{y=b} h(x, y) \quad (1)$$

$$S(x, y) = h(x, y) - Gray_{AVE}$$

$$G(x, y) = g(x, y) + S(x, y),$$

where a and b are respectively the length and the width of the imaging scope in pixels (2) The relationship between basic weights and transmittance (referring to FIG. 4) From the exponential law of absorption, we can obtain the relationship between basic weights and transmittance with respect to the image taken by a camera as follows.

$$\frac{I_{ij}}{I_o} = e^{-\alpha h_{ij} d_{ij}} \quad (2)$$

where $I_{ij}$ is the intensity of incident light beams at the position (i, j) of a pixel on an image.

$I_o$=the intensity of emission light beams $\alpha$=the absorption coefficient of materials $h_{ij}$=the thickness of the object to be measured $d_{ij}$=the density of the material to be measured For the local images taken by the camera, the weight $W_{ij}$ per unit area $A_{ij}$ of a pixel is:

$$W_{ij}=d_{ij}h_{ij}A_{ij} \qquad (3)$$

The weight $W_{ij}$ per unit area $A_{ij}$ of a pixel can be expressed as a function of $I_{ij}$ by means of the equations (2) and (3).

$$W_{ij} = \frac{1}{\alpha}\ln\left(\frac{I_o}{I_{ij}}\right)A_{ij} \qquad (4)$$

Hence, the weight $W_{ij}$ per unit area $A_{ij}$ of the local images taken by the camera is:

$$W = \frac{1}{\alpha}\sum_{i=1}^{a}\sum_{j=1}^{b}\ln\left(\frac{I_o}{I_{ij}}\right)A_{ij} = \frac{A}{\alpha}\overline{\ln\left(\frac{I_o}{I_{ij}}\right)} \qquad (5)$$

The average weight of the local area is:

$$\overline{W} = \frac{1}{\alpha}\sum_{i=1}^{a}\sum_{j=1}^{b}\ln\left(\frac{I_o}{I_{ij}}\right)A_{ij} / \sum_{i=1}^{a}\sum_{j=1}^{b}A_{ij} = \frac{1}{\alpha}\overline{\ln\left(\frac{I_o}{I_{ij}}\right)} \qquad (6)$$

where a and b are respectively the length and the width of the imaging scope in pixels.

Figure 6:
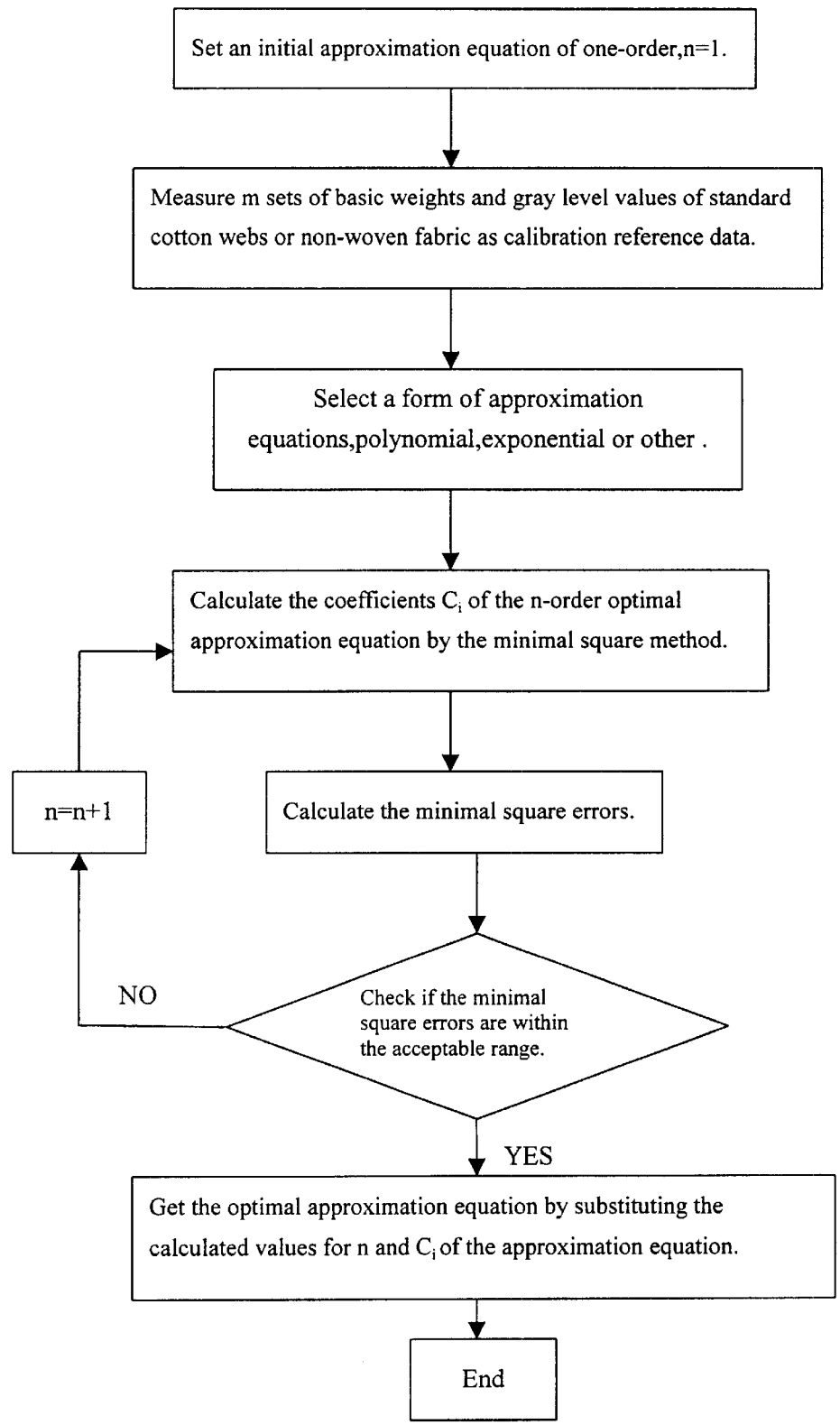
FIG. 6 is a flow chart showing the steps of calculating approximate curves by the minimum square method according to the invention.

(3) The derivation of an optimal approximation equation representing the relationship between transmittance and basic weights by the minimum square method (referring to FIG. 6)

When cotton webs made of the same material is to be measured, $\alpha$ is a constant. If the intensity of the light source does not change, $I_o$ is a constant. Thus, from the equation (6), it is evident that the basic weights only relate to the light intensity (or gray level values) that the sensor receives. The intensity of light rays the sensor detects is proportional to the gray level values according to a experiment result.

Therefore, the equation (6) can be converted by the minimum square method of numerical analysis as follows $$\overline{W} = \frac{1}{\alpha}\overline{\ln\frac{I_o}{I_{ij}}} = C_i f_i(X) = C_1 + C_2 X + C_3 X^2 + \ldots + C_n X^{n-1} \qquad (7)$$

where $C_i$ is the coefficient to be determined, X is the average gray level value of the local image taken by the camera and is inversely proportional to $$\ln\left(\frac{I_o}{I_{ij}}\right),$$

$\alpha$ and $I_o$ are constants, and f(x) is an approximation equation, which may be a combination of any orthogonal basis equations and can be best illustrated as follows.

$$\begin{bmatrix} m & \sum_{i=1}^{m}X_i & \sum_{i=1}^{m}X_i^2 & \ldots & \sum_{i=1}^{m}X_i^{n-1} \\ \sum_{i=1}^{m}X_i & \sum_{i=1}^{m}X_i^2 & \sum_{i=1}^{m}X_i^3 & \ldots & \sum_{i=1}^{m}X_i^n \\ \sum_{i=1}^{m}X_i^2 & \sum_{i=1}^{m}X_i^3 & \sum_{i=1}^{m}X_i^4 & \ldots & \sum_{i=1}^{m}X_i^{n+1} \\ \vdots & \vdots & \vdots & & \vdots \\ \sum_{i=1}^{m}X_i^{n-1} & \sum_{i=1}^{m}X_i^n & \sum_{i=1}^{m}X_i^{n+1} & \ldots & \sum_{i=1}^{m}X_i^{2(n-1)} \end{bmatrix} \begin{bmatrix} C_1 \\ C_2 \\ C_3 \\ \vdots \\ C_n \end{bmatrix} = \begin{bmatrix} \sum_{i=1}^{m}\overline{W}_i \\ \sum_{i=1}^{m}X_i\overline{W}_i \\ \sum_{i=1}^{m}X_i^2\overline{W}_i \\ \vdots \\ \sum_{i=1}^{m}X_i^{n-1}\overline{W}_i \end{bmatrix} \qquad (8)$$

Thus a mathematical equation with a form of matrix (8) and the coefficient $C_i$ can be obtained from measured values of m standard samples, the relationship between average gray level values X and basic weights $\overline{W}_i$ as well as n-order polynomial equations by the minimum square method. Furthermore, the optimal value of n is obtained by the minimum square error equation (8).

$$L = \sum_{i=1}^{m}e_i^2 = \qquad (9)$$

$$\sum_{i=1}^{m}(\overline{W_i^a} - \overline{W_i})^2 = \sum_{i=1}^{m}(\overline{W_i^a} - C_1 - C_2 X_i - C_3 X_i^2 - \ldots - C_n X_i^{n-1})^2$$

where $\overline{W_i}$ is the average basic weight measured from the i-th sample and $\overline{W_{i^a}}$ is the actual average value of the basic weight of the i-th sample.

From the errors in L when n=1, 2, and so on, the optimal values of n and $C_i$ can be obtained by the following two methods.

Method 1: n and $C_i$ are the values when L is the minimum.

Method 2: n and C are the values when L is smaller than a preset error limit.

These values are substituted into the equation. (7) to generate an optimal approximation equation of the system.

Figure 7:
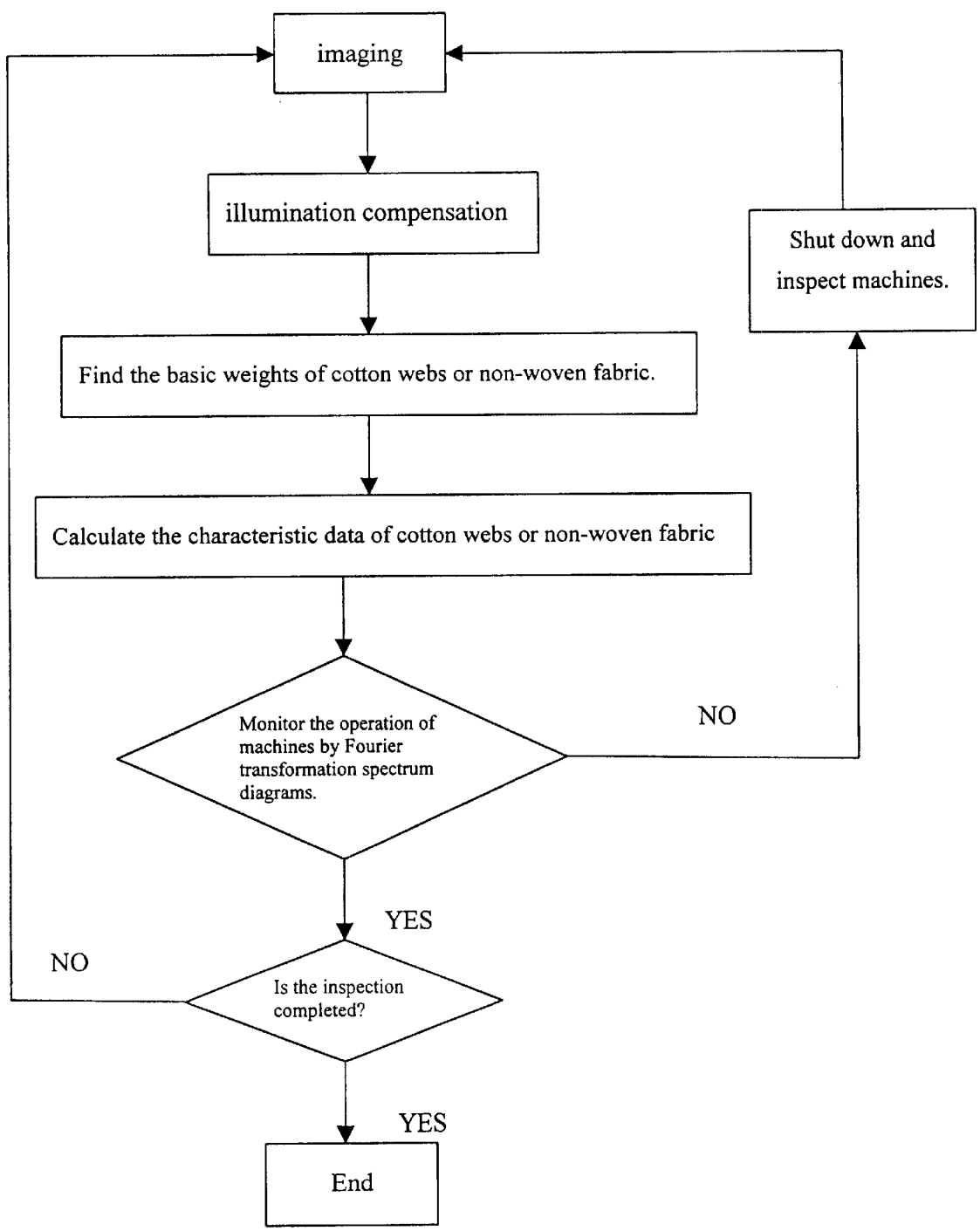
FIG. 7 is a flow chart showing the inspection method according to the invention.

(4) Evaluation of the basic weights of cotton webs (referring to FIG. 7) When executing an inspection of cotton webs by the system according to the invention, the basic weights of cotton webs can be obtained from a conversion of the average gray level values $X_i$ by using the optimal approximation equation (7).

(5) Calculation of the characteristic data of cotton webs (referring to FIG. 7) Through a dynamic inspection and collected data, the homogeneity variable of cotton webs and the statistical possibility of basic weights can be obtained from:

$$CV \% = \frac{100}{\overline{W_t}} \cdot \sqrt{\frac{1}{N}\sum_{i=1}^{N}(\overline{W_t} - \overline{W_i})^2} \qquad (10)$$

$$\overline{W_i} = \sum_{i=1}^{N} \overline{W_i}/N \qquad (11)$$

$$P(W_i) = \frac{n_i}{N} \qquad (12)$$

where CV % is the homogeneity variable, $W_t$ is the average value of the basic weights in a dynamic sampling in a time range from 0 to t, N is the total dynamic sampling number in a time range from 0 to t, n is the number of the basic weight i, and $P(W_i)$ is the possibility of the basic weight i.

(6) Monitoring the operation of machines by a Fourier transformation spectrum diagram The system according to the invention uses a Fourier transformation spectrum diagram of basic weights to examine if an abnormal frequency happens so as to determine whether machines run abnormally or a periodical inhomogeneity happens. The formula is as follows.

$$W(u) = \frac{1}{M}\sum \overline{W}(x)\exp(-2\pi u x j/M) = R(u) + jI(u) \qquad (13)$$

$$|W(u)| = [R^2(u) + I^2(u)]^{1/2} \qquad (14)$$

where W(x) is the average basic weight value of the x-th images, W(u) is a Fourier transformation function, R(u) is the real part of W(u) and I(u) is the imaginary part of W(u), and |W(u)| is Fourier spectrum.

From the described above, the on-line inspection system of the homogeneity of cotton webs according to the invention has practical value in the industry. Its advantages are summarized as follows.

(1) The system according to the invention performs non-contact inspections and so it will not bring any harmful influence to the physical properties of cotton webs.
(2) The samples taken by the inspection system according to the invention are two-dimensional areas, which has more representation than spot sampling taken by a prior art inspection system and can minimize the influence of variations at small areas on an overall homogeneity inspection.
(3) The system of the invention can perform a Fourier transform of homogeneity data so as to monitor production operation to see if any abnormal condition or periodical inhomogeneity occur.
(4) The system according to the invention can perform longitudinal and transversal inspections by using more cameras arranged in transversal direction. Thus inspectors can more closely monitor the overall production situation and trace the causes of abnormal homogeneity variations.
(5) The system of the invention can generate overall homogeneity distribution diagrams and conduct variation analysis on the basis of collected data.
(6) The system of the invention can display the relationship among measured homogeneity data, standard values, and tolerances (upper and lower limits). When homogeneity exceeds preset limits, the system emits alert signals so as to facilitate the control of quality and display on screen the continuous variations in basic weight and thickness.

The concept and techniques of the invention have never seen in the field before. Obviously the method and the system according to the invention can achieve the effects of correctly detecting the homogeneity of cotton webs and promoting production efficiency and quality set forth at the beginning of the description, and has useful value in the industry. It meets the essence of a patent and thus we hereby apply for a patent grant.

The above description of preferred embodiments serves only to explain the features and advantages of the invention. The invention is not intended to be limited thereby. Those skilled in the are can make modifications and changes without departing from the scope of the invention. It is to be understood that all such equivalent structures are to be included within the scope of the following claims.

What is claimed is:

1. An on-line cotton web homogeneity inspection method using a digital image processing technique characterized in that an mathematical equation representing the relationship between transmittance of cotton webs and its basic weight can be acquired by a video camera and a light source, and in that an optimal approximation equation results from data collected and processed by a computer by means of optical principles and numerical analysis, and in that in on-line tests the transmittance measured by said computer is converted by said optimal approximation equation into basic weight variation charts, including a CV % dynamic curve chart, a basic weight statistic chart, a basic weight control chart and a basic weight dynamic curve chart, and in that said computer generates a Fourier transformation spectrum diagram on the basis of the variations of cotton web homogeneity, from which spectrum diagram said computer can detect any abnormal operation and periodical variations of machines.

2. The method as claimed in claim 1 characterized in that said method can be used to monitor the manufacturing processes of cotton webs, non-woven fabric and paper.

3. The method as claimed in claim 1 characterized in that through a variable CV % dynamic chart said method can detect the deviation of basic weights (or homogeneity) of cotton webs in process to facilitate production quality control.

4. The method as claimed in claim 1 characterized in that said method can detect the basic weight range of cotton webs through a basic weight statistic chart so as to facilitate production quality control.

5. The method as claimed in claim 1 characterized in that through said basic weight control chart said system can detect any basic weights that are out of a preset range and that can send out alert signals when basic weights are over the range so that operators can take a close look at the whole production procedure and find the root causes.

6. The method as claimed in claim 1 characterized in that through said basic weight dynamic chart users can find the basic weight difference between the current tested spot and the previous tested spot so that it is much easier for production quality control.

7. The method as claimed in claim 1 characterized in that through Fourier transformation a Fourier spectrum chart can be generated, which shows abnormal wave peaks when production equipment malfunctions and by means of which users can detect periodical abnormal operations.

8. The method as claimed in claim 1 characterized in that said method can detect cotton web homogeneity variations in both longitudinal and transverse directions by a plurality of cameras arranged along these two directions.

9. The method as claimed in claim 1 characterized in that through a suitable combination of different cameras and light sources having various wavelengths said method can be used on basic weight or homogeneity tests for different materials.

10. The method as claimed in claim 1 characterized in that by setting the imaging aperture of said cameras the sizes and locations of samples can be adjusted to make measured data more representative.

11. The method as claimed in claim 1 characterized in that said method makes use of a standard gray level plate and takes its image as a standard, with an imaging area of a pixels in length and b pixels in width.

12. The method as claimed in claim 1 characterized in that a relationship between transmittance and basic weights can be obtained by means of the exponential law of absorption and an average basic weight over a local area can be calculated from a unit area of a pixel and the basic weights of local images.

13. The method as claimed in claim 1 characterized in that a relationship between the transmittance and the basic weights of cotton webs can be obtained by means of the minimum square method.

14. The method as claimed in claim 1 characterized in that the basic weight of examined cotton webs can be obtained through a conversion by an optimal approximation equation representing the relationship between average gray level values and basic weights.

15. The on-line cotton web homogeneity inspection system using a digital image processing technique comprising a light source, a CCD camera, an image pickup card, and a personal computer; said CCD camera being used to take image data as cotton webs to be examined are passed between said CCD camera and said light source, said image pickup card storing the image data, and said computer being used to calculate and analyze the image data, and storing and displaying the results on an output device, said computer being operable to derive responsive to said calculation and analysis of the image data a basic weight parameter for the cotton webs, said output device being selectively configurable by said computer to display at least one of a plurality of predetermined basic weight variation charts, said predetermined basic weight variation charts including: a variable CV % dynamic curve chart, a basic weight statistic chart, a basic weight variation control chart, a basic weight dynamic curve chart, and a Fourier transformation spectrum diagram chart.

* * * * *